(12) United States Patent
Thaimattam et al.

(10) Patent No.: US 12,065,426 B2
(45) Date of Patent: Aug. 20, 2024

(54) CRYSTALLINE FORM OF NILOTINIB HYDROCHLORIDE, PROCESS FOR ITS PREPARATION AND PHARMACEUTICAL COMPOSITION CONTAINING THE SAME

(71) Applicant: Laurus Labs Limited, Hyderabad (IN)

(72) Inventors: Ram Thaimattam, Hyderabad (IN); Suresh Babu Radhakrishnan, Hyderabad (IN); Nageswara Rao Regandla, Hyderabad (IN); Venkata Lakshmi Narasimha Rao Dammalapati, Hyderabad (IN); Uma Maheswer Rao Vasireddi, Hyderabad (IN)

(73) Assignee: LAURUS LABS LIMITED, Hyderabad (IN)

( * ) Notice: Subject to any disclaimer, the term of this patent is extended or adjusted under 35 U.S.C. 154(b) by 456 days.

(21) Appl. No.: 17/283,410

(22) PCT Filed: Nov. 5, 2019

(86) PCT No.: PCT/IB2019/059469
§ 371 (c)(1),
(2) Date: Apr. 7, 2021

(87) PCT Pub. No.: WO2020/095187
PCT Pub. Date: May 14, 2020

(65) Prior Publication Data
US 2021/0380557 A1  Dec. 9, 2021

(30) Foreign Application Priority Data
Nov. 5, 2018  (IN) .............................. 201841041777

(51) Int. Cl.
*C07D 401/14* (2006.01)
(52) U.S. Cl.
CPC ........ *C07D 401/14* (2013.01); *C07B 2200/13* (2013.01)
(58) Field of Classification Search
CPC ... A61K 31/506; A61P 35/02; C07B 2200/13; C07D 401/14
See application file for complete search history.

(56) References Cited

U.S. PATENT DOCUMENTS

| 8,163,904 | B2 | 4/2012 | Manley et al. |
| 8,703,788 | B2 | 4/2014 | Reddy et al. |
| 9,090,598 | B2 | 7/2015 | Piran et al. |
| 9,981,947 | B2 | 5/2018 | Peddy et al. |
| 2013/0245052 | A1* | 9/2013 | Reddy .................. C07D 401/14 514/275 |

FOREIGN PATENT DOCUMENTS

| WO | WO 2007/015870 A2 | 2/2007 | |
| WO | WO-2010054056 A2 * | 5/2010 | ........... C07D 401/14 |
| WO | WO 2014/059518 A9 | 4/2014 | |
| WO | WO-2016020891 A1 * | 2/2016 | ........... C07D 401/04 |

OTHER PUBLICATIONS

Search Report and Written Opinion from PCT/IB2019/059469.

* cited by examiner

*Primary Examiner* — San Ming R Hui
*Assistant Examiner* — Padmaja S Rao
(74) *Attorney, Agent, or Firm* — Blank Rome LLP

(57) ABSTRACT

The present invention relates to novel crystalline form of nilotinib hydrochloride, process for its preparation and pharmaceutical composition comprising the same.

12 Claims, 10 Drawing Sheets

CRYSTALLINE FORM OF NILOTINIB HYDROCHLORIDE, PROCESS FOR ITS PREPARATION AND PHARMACEUTICAL COMPOSITION CONTAINING THE SAME

CROSS-REFERENCE TO RELATED APPLICATIONS

This is a national phase application that is based on and claims the benefit of International Application No. PCT/IB2019/059469, filed on Nov. 5, 2019, which is based on and claims the benefit of the filing date and disclosure of Indian Provisional Application No. 201841041477, filed on Nov. 5, 2018, the contents of which are incorporated by reference herein.

FIELD OF THE INVENTION

The present invention relates to novel crystalline form of Nilotinib hydrochloride, process for its preparation and pharmaceutical composition containing the same.

BACKGROUND OF THE INVENTION

Nilotinib hydrochloride is chemically known as 4-methyl-N-[3-(4-methyl-1H-imidazol-1-yl)-5-(trifluoromethyl)phenyl]-3-[[4-(3-pyridinyl)-2-pyrimidinyl] amino]-benzamide hydrochloride and represented by the following structural Formula-I:

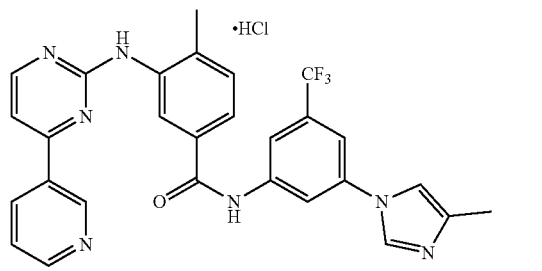

Formula-I

Nilotinib is a tyrosine kinase inhibitor used for the treatment of drug-resistant chronic myelogenous leukemia (CML), and in particular, for the treatment of chronic phase and accelerated phase Philadelphia chromosome positive chronic myeloid leukemia (CML) in adult patients whose disease has progressed on or who cannot tolerate other therapies that included imatinib. Nilotinib is administrated as a hydrochloride salt in the form of capsules that are marketed in the USA and the EU under the name Tasigna®.

Nilotinib and process for its preparation was first disclosed in WO2004005281. Later published PCT publication No. WO2007015871 discloses hydrochloride, monophosphate, diphosphate, sulphate, methane sulfonate, ethane sulfonate, benzene sulfonate and p-toluene sulfonate salts of nilotinib, their process and composition comprising them.

PCT publication No. WO2007015870 discloses crystalline forms of nilotinib hydrochloride designated as Form A, Form A', Form A", Form B, Form B', Form C, Form C', Form D, Form $S_B$, Form $S_B'$, Form $S_C$, Form $S_E$, and amorphous form of nilotinib hydrochloride. Further, it also discloses substantially pure crystalline Form A and Form B of nilotinib free base and process for its preparation.

PCT publication No. WO2010054056 discloses polymorphic forms of nilotinib hydrochloride designated as Form T1, Form T2, Form T3, Form T4, Form T5, Form T6, Form T7, Form T8, Form T9, Form T10, Form T11, Form T12, Form T13, Form T14, Form T15, Form T16, Form T17, Form T18 and Form T19.

PCT publication No. WO2011086541 discloses crystalline form of nilotinib hydrochloride monohydrate and process for its preparation.

PCT publication No. WO2011163222 discloses crystalline forms of nilotinib hydrochloride designated as Form T20, Form T27, Form T28 and Form T29.

PCT publication No. WO2012070062 crystalline form H1 of nilotinib hydrochloride and process for its preparation.

U.S. Pat. No. 9,440,959 discloses crystalline form of nilotinib hydrochloride dihydrate and process for its preparation.

Indian patent publication No. 3836/CHE/2014 discloses crystalline form M and Form S of nilotinib hydrochloride and process for their preparation.

IP.COM journal IPCOM000187328 discloses crystalline forms T7, T8, T10, T14-16 of Nilotinib hydrochloride and process for their preparation.

IP.COM journal IPCOM000183524 discloses crystalline forms T2-T6, T9 and T11-T13 of nilotinib hydrochloride and process for their preparation.

IP.COM journal IPCOM000193749 discloses crystalline forms T24, T25 and T26 of nilotinib hydrochloride and process for their preparation.

IP.COM journal IPCOM000190565 discloses crystalline forms T21-T23 of nilotinib hydrochloride and process for their preparation.

IP.COM journal IPCOM000195326 discloses crystalline form T5 of nilotinib hydrochloride and process for its preparation.

Polymorphism is the occurrence of different crystalline forms of a single compound and it is a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as different solubility profiles, different melting point temperatures and/or different x-ray diffraction peaks. Since the solubility of each polymorph may vary, identifying the existence of pharmaceutical polymorphs is essential for providing pharmaceuticals with predicable solubility profiles. It is desirable to investigate all solid state forms of a drug, including all polymorphic forms and solvates, and to determine the stability, dissolution and flow properties of each polymorphic form.

Polymorphic forms and solvates of a compound can be distinguished in a laboratory by X-ray diffraction spectroscopy and by other methods such as, infrared spectrometry. Additionally, polymorphic forms and solvates of the same drug substance or active pharmaceutical ingredient, can be administered by itself or formulated as a drug product (also known as the final or finished dosage form), and are well known in the pharmaceutical art to affect, for example, the solubility, stability, flowability, tractability and compressibility of drug substances and the safety and efficacy of drug products.

The discovery of new crystalline polymorphic forms and solvates of a pharmaceutically useful compound, like nilotinib hydrochloride, may provide a new opportunity to improve the performance characteristics of a pharmaceutical product. It also adds to the material that a formulation scientist has available for designing, for example, a pharmaceutical dosage form of a drug with a targeted release profile or other desired characteristic.

In the pharmaceutical industry, there is a constant need to identify critical physiochemical parameters such as novel polymorphic forms or salts that affect the drug's performance, stability, etc., and which may play a key role in determining a drug's market acceptance and success. Nilotinib hydrochloride is one of the important drug available in the market for the treatment of chronic myelogenous leukemia. Hence, it's important to discover new polymorphic forms of nilotinib hydrochloride, which may provide a new opportunity to improve the performance characteristics of a pharmaceutical product. There therefore remains a need for novel polymorphic forms of nilotinib hydrochloride with improved characteristics.

Hence the main objective of the present invention is to provide novel crystalline form of nilotinib hydrochloride.

SUMMARY OF THE INVENTION

Accordingly, the present invention provides novel crystalline form of nilotinib hydrochloride, process for its preparation and pharmaceutical composition comprising the same. The novel crystalline form of nilotinib hydrochloride of the present invention have advantageous properties selected from at least one of: chemical purity, flowability, solubility, morphology or crystal habit, stability—such as storage stability, stability to dehydration, and stability to polymorphic conversion, low hygroscopicity, and low content of residual solvents.

In one embodiment, the present invention provides novel crystalline form of nilotinib hydrochloride, which is herein designated as Nilotinib hydrochloride Form L.

In another embodiment, the present invention provides nilotinib hydrochloride Form L characterized by a powder X-Ray diffraction pattern having one or more peaks at about 4.9, 5.5, 6.9, 8.9, 9.1, 9.9, 11, 12.3, 13.3, 13.8, 14.9, 15.7, 16.5, 17.8, 19.3, 19.9, 20.3, 21.1, 21.5, 22.0, 22.9, 23.3, 24.8, 25.5, 26.0, 26.6, 27.6, 28.7, 29.5, 31.3, 33.7, 34.7, 35.5, 36.3 and 37.6° 2θ, where all the peak values listed are ±0.2° 2θ.

In another embodiment, the present invention provides nilotinib hydrochloride Form L characterized by a powder X-Ray diffraction pattern having one or more peaks at about 4.9, 5.5, 6.9, 8.9, 9.9, 11, 12.3, 13.3, 14.9, 15.7, 17.8, 19.3, 19.9, 20.3, 21.1, 21.5, 22.0, 22.9, 23.3, 24.8, 25.5, 26.0, 26.6, 27.6, 28.7, 29.5, 31.3, 33.7, 34.7, 35.5, 36.3 and 37.6° 2θ, where all the peak values listed are ±0.2° 2θ.

In another embodiment, the present invention provides nilotinib hydrochloride Form L characterized by a powder X-Ray diffraction pattern having one or more peaks at about 4.9, 5.5, 8.9, 9.9, 11, 13.3, 17.8, 19.9, 21.1, 21.5, 22.9, 26.6, 27.6, 28.7 and 29.5° 2θ, where all the peak values listed are ±0.2° 2θ.

In another embodiment, the present invention provides nilotinib hydrochloride Form L characterized by a powder X-Ray diffraction (PXRD) pattern substantially in accordance with FIG. 1.

In another embodiment, the present invention provides nilotinib hydrochloride Form L characterized by a powder X-Ray diffraction (PXRD) pattern substantially in accordance with FIG. 4.

In another embodiment, the present invention provides nilotinib hydrochloride Form L characterized by a differential scanning calorimetry (DSC) substantially in accordance with FIG. 2.

In another embodiment, the present invention provides nilotinib hydrochloride Form L characterized by a differential scanning calorimetry (DSC) substantially in accordance with FIG. 5.

In another embodiment, the present invention provides nilotinib hydrochloride Form L characterized by a differential scanning calorimetry (DSC) having three endothermic peaks at about 89.5° C., 204.3° C. and 225° C.

In another embodiment, the present invention provides nilotinib hydrochloride Form L characterized by a differential scanning calorimetry (DSC) having three endothermic peaks at about 95° C., 203° C. and 224.7° C.

In another embodiment, the present invention provides nilotinib hydrochloride Form L characterized by a thermogravimetric analysis (TGA) substantially in accordance with FIG. 3.

In another embodiment, the present invention provides nilotinib hydrochloride Form L characterized by a thermogravimetric analysis (TGA) showing weight loss of about 2.3%.

In another embodiment, the present invention provides nilotinib hydrochloride Form L characterized by a Fourier-transform Infrared (FTIR) spectrum substantially in accordance with FIG. 6.

In another embodiment, the present invention provides nilotinib hydrochloride Form L characterized by Fourier-transform Raman spectrum substantially in accordance with FIG. 7.

In another embodiment, the present invention provides nilotinib hydrochloride Form L characterized by data selected from the group comprising: a powder X-Ray diffraction (PXRD) pattern substantially in accordance with FIG. 4; a differential scanning calorimetry (DSC) substantially in accordance with FIG. 2; a thermogravimetric analysis (TGA) substantially in accordance with FIG. 3; and combinations thereof.

In another embodiment, the present invention provides nilotinib hydrochloride Form L characterized by data selected from the group comprising: a powder X-Ray diffraction (PXRD) pattern substantially in accordance with FIG. 4; a differential scanning calorimetry (DSC) substantially in accordance with FIG. 5; a thermogravimetric analysis (TGA) substantially in accordance with FIG. 3; and combinations thereof.

In another embodiment, the present invention provides a process for the preparation of nilotinib hydrochloride Form L, which comprises of
  a) dissolving nilotinib in a mixture of formic acid and ethylformate at a suitable temperature,
  b) adding hydrochloric acid to step a) solution at a suitable temperature, and
  c) isolating nilotinib hydrochloride Form L.

In another embodiment, the present invention provides a pharmaceutical composition comprising novel crystalline nilotinib hydrochloride Form L of the present invention and at least one pharmaceutically acceptable excipient.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
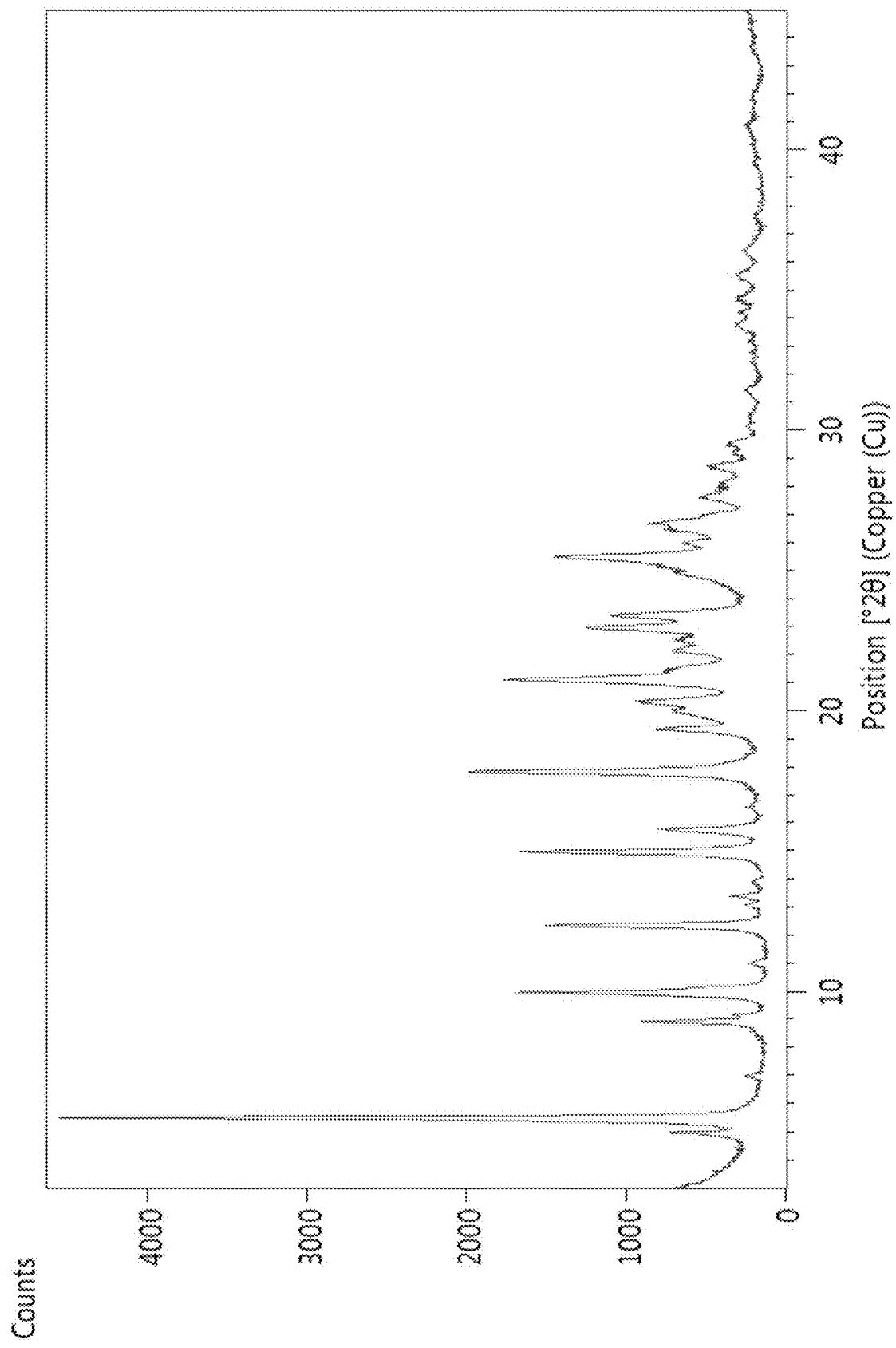
FIG. 1 is the characteristic powder X-ray diffraction (XRD) pattern of a nilotinib hydrochloride Form L.

The present invention provides novel crystalline form of nilotinib hydrochloride, process for its preparation and pharmaceutical composition comprising the same.

The nilotinib hydrochloride Form L of the present invention are characterized by one or more analytical methods such as X-ray powder diffraction (XRPD) patterns, Differential scanning calorimetry (DSC), Fourier-transform Infrared (FTIR) spectrum, Fourier-transform Raman spectrum and Thermogravimetric analysis (TGA).

The X-Ray powder diffraction data in the present invention was measured using PANalytical X'pert$^3$ X-ray powder diffractometer equipped with a Cu-anode ([λ]=1.54 Angstrom), X-ray source operated at 45 kV, 40 mA. The sample was analysed using the following instrument parameters: measuring range=3-45° 2θ; step size=0.01°; and Time per step=50 sec.

The differential scanning calorimetry (DSC) data in the present invention was acquired using TA instruments DSC Q200 Differential Scanning calorimeter with universal Analysis 2000 software under the following conditions; Heating rate: 10° C./minute; Equilibration temperature: 25° C.; Temperature range: 25° C.-300° C.; Type of pan: hermetic pan with pin hole; Nitrogen flow: 50 mL/minute.

Thermogravimetry analysis (TGA) data in the present invention was acquired using TA instruments TGA Q500 thermogravimetric analyser with universal Analysis 2000 software using the following conditions; Heating rate: 10° C./min; Temperature range: 28±2° C.-250° C.; Nitrogen flow: 60 mL/minute.

Fourier-transform infrared (FTIR) spectroscopy data in the present invention was acquired using Perkin Elmer Spectrum 100 FTIR spectrometer using the following conditions; Sample preparation: Nujol; Resolution: 4 cm$^{-1}$; Number of scans: 4; Wave number range: 4000 to 650 cm$^{-1}$.

Fourier-transform Raman spectroscopy data in the present invention was acquired using Brucker MultiRAM FT-Raman spectrometer under the following conditions: Laser Power: 300 mW; Laser wave number: 1064 cm$^{-1}$; wave number range: 3600 to 50 cm$^{-1}$; Resolution: 4 cm$^{-1}$; Scan time: 3 mins.

Dynamic vapour sorption (DVS) data in the present invention was acquired using TA instruments TA Q5000SA Dynamic vapour sorption analyser with Universal Analysis 2000 software under following parameters; Sample was initially equilibrated at 0% RT for 120 mins; humidity range: 10 to 90%; humidity step size: 10%; Equilibration condition: change in mass less than 0.01% within 5 mins.

In one embodiment, the present invention provides novel crystalline form of nilotinib hydrochloride, which is herein designated as Nilotinib hydrochloride Form L.

In another embodiment, the present invention provides nilotinib hydrochloride Form L characterized by a powder X-Ray diffraction pattern having one or more peaks at about 4.9, 5.5, 6.9, 8.9, 9.1, 9.9, 11, 12.3, 13.3, 13.8, 14.9, 15.7, 16.5, 17.8, 19.3, 19.9, 20.3, 21.1, 21.5, 22.0, 22.9, 23.3, 24.8, 25.5, 26.0, 26.6, 27.6, 28.7, 29.5, 31.3, 33.7, 34.7, 35.5, 36.3 and 37.6° 2θ, where all the peak values listed are ±0.2° 2θ.

In a specific embodiment, the present invention provides nilotinib hydrochloride Form L characterized by a powder X-Ray diffraction pattern having one or more peaks at about 4.9, 5.5, 6.9, 8.9, 9.9, 11, 12.3, 13.3, 14.9, 15.7, 17.8, 19.3, 19.9, 20.3, 21.1, 21.5, 22.0, 22.9, 23.3, 24.8, 25.5, 26.0, 26.6, 27.6, 28.7, 29.5, 31.3, 33.7, 34.7, 35.5, 36.3 and 37.6° 2θ, where all the peak values listed are ±0.2° 2θ.

In a further specific embodiment, the present invention provides nilotinib hydrochloride Form L characterized by a powder X-Ray diffraction pattern having one or more peaks at about 4.9, 5.5, 8.9, 9.9, 11, 13.3, 17.8, 19.9, 21.1, 21.5, 22.9, 26.6, 27.6, 28.7 and 29.5° 2θ, where all the peak values listed are ±0.2° 2θ.

In another embodiment, the present invention provides nilotinib hydrochloride Form L characterized by a powder X-Ray diffraction (PXRD) pattern substantially in accordance with FIG. 1.

Figure 4:
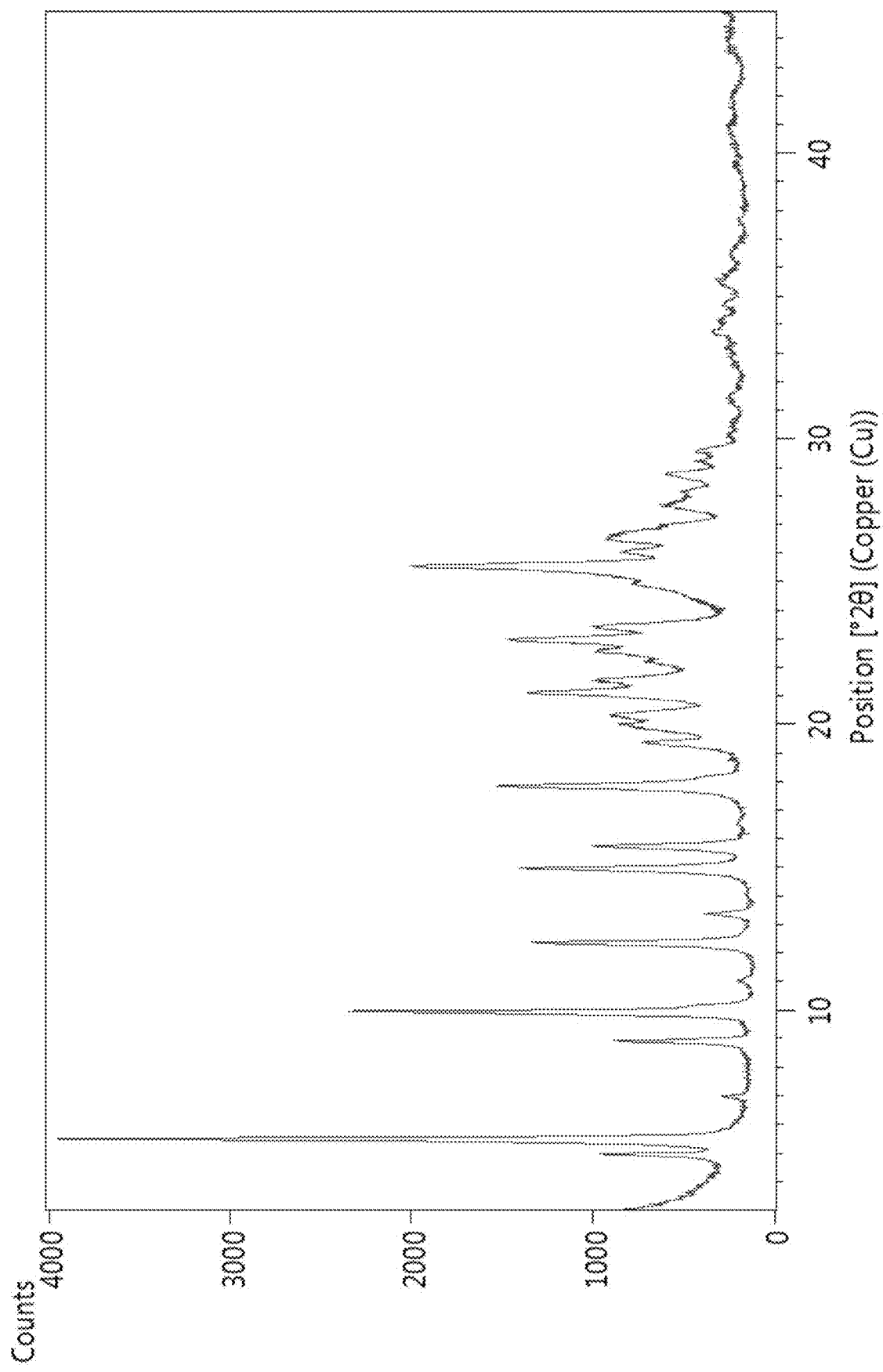
FIG. 4 is the characteristic powder X-ray diffraction (XRD) pattern of a nilotinib hydrochloride Form L.

In another embodiment, the present invention provides nilotinib hydrochloride Form L characterized by a powder X-Ray diffraction (PXRD) pattern substantially in accordance with FIG. 4.

Figure 2:
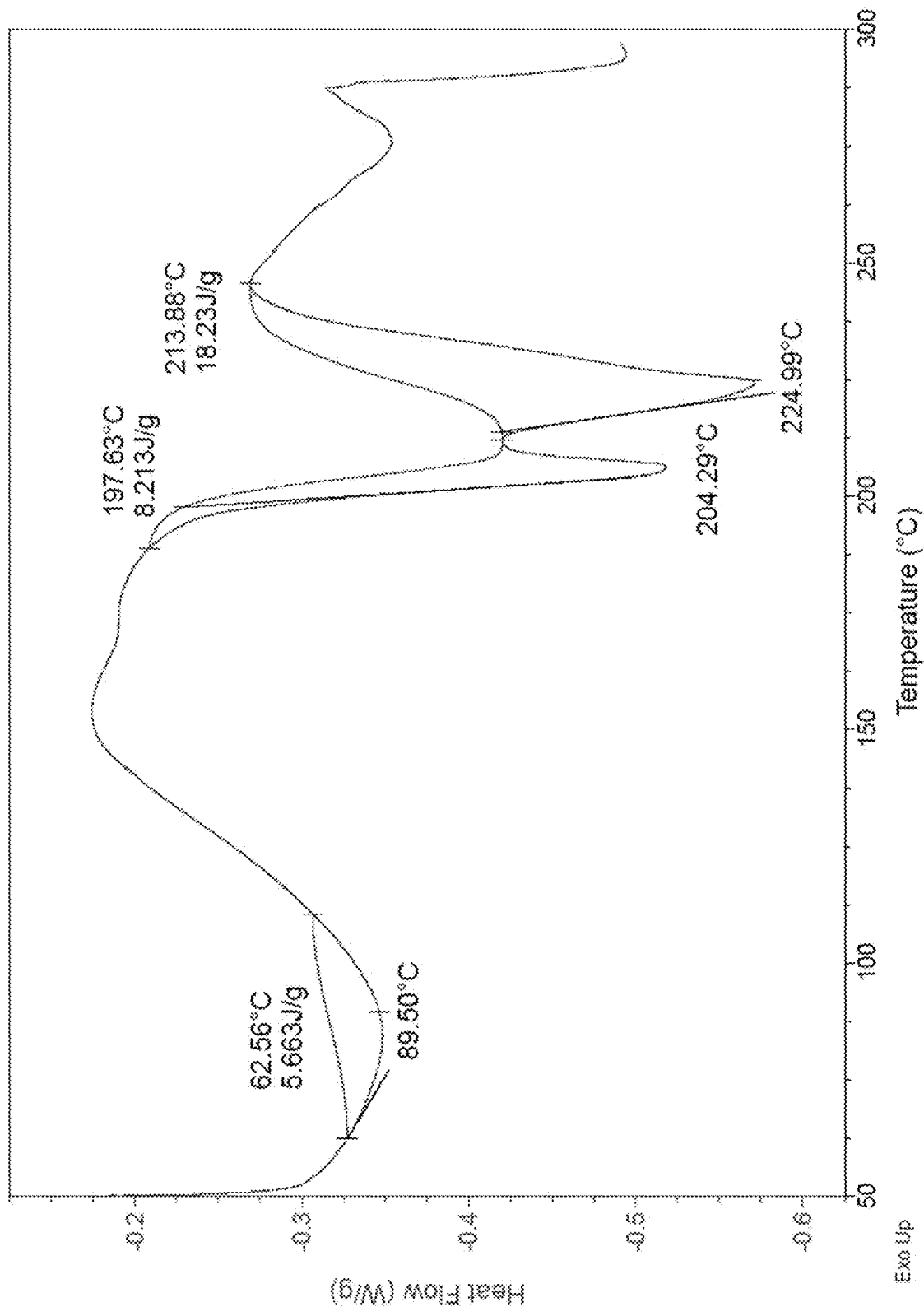
FIG. 2 is the characteristic differential scanning calorimetric (DSC) thermogram of nilotinib hydrochloride Form L.

In another embodiment, the present invention provides nilotinib hydrochloride Form L characterized by a differential scanning calorimetry (DSC) substantially in accordance with FIG. 2.

Figure 5:
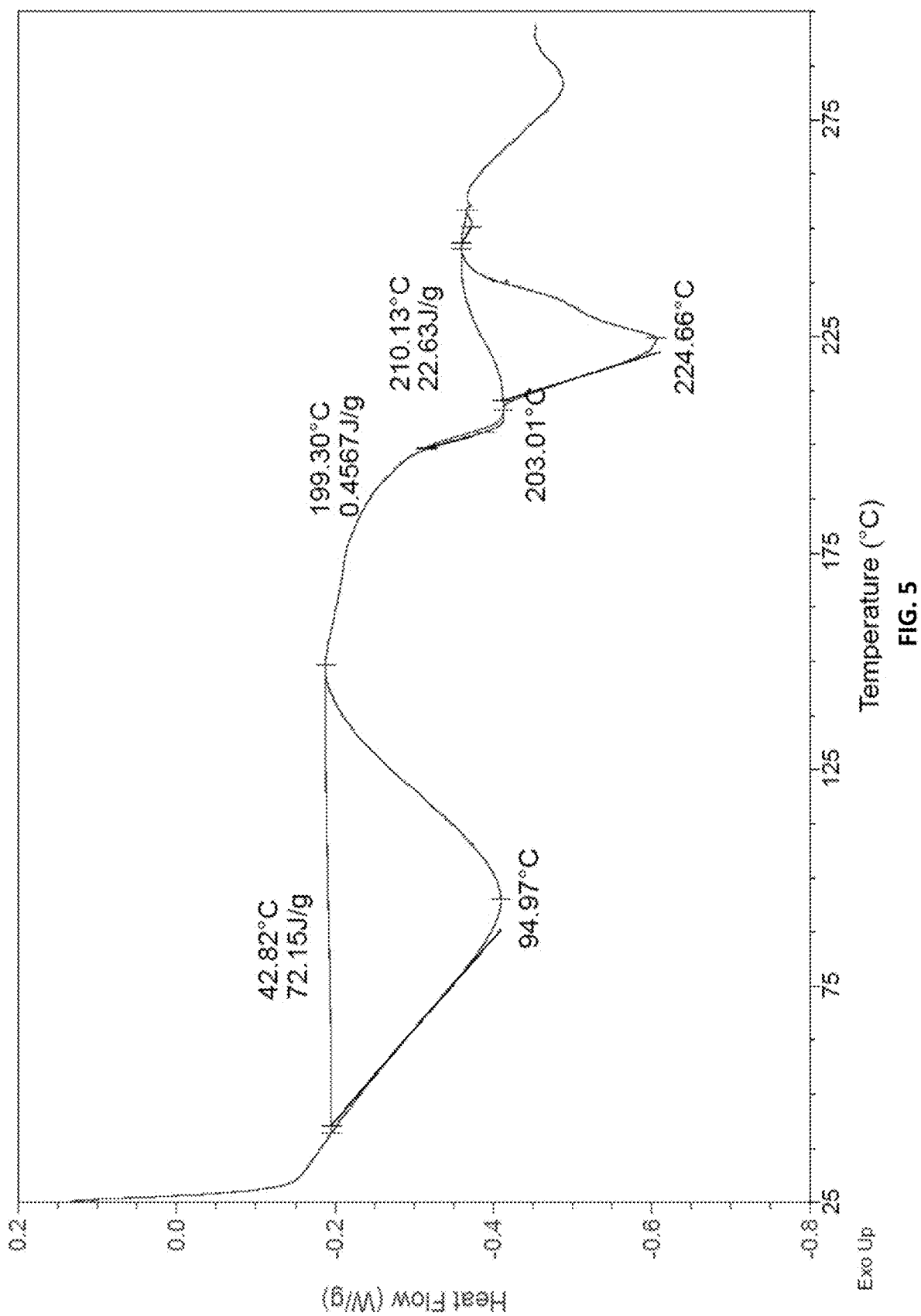
FIG. 5 is the characteristic differential scanning calorimetric (DSC) thermogram of nilotinib hydrochloride Form L.

In another embodiment, the present invention provides nilotinib hydrochloride Form L characterized by a differential scanning calorimetry (DSC) substantially in accordance with FIG. 5.

In another embodiment, the present invention provides nilotinib hydrochloride Form L characterized by a differential scanning calorimetry (DSC) having three endothermic peaks at about 89.5° C., 204.3° C. and 225° C.

In another embodiment, the present invention provides nilotinib hydrochloride Form L characterized by a differential scanning calorimetry (DSC) having three endothermic peaks at about 95° C., 203° C. and 224.7° C.

Figure 3:
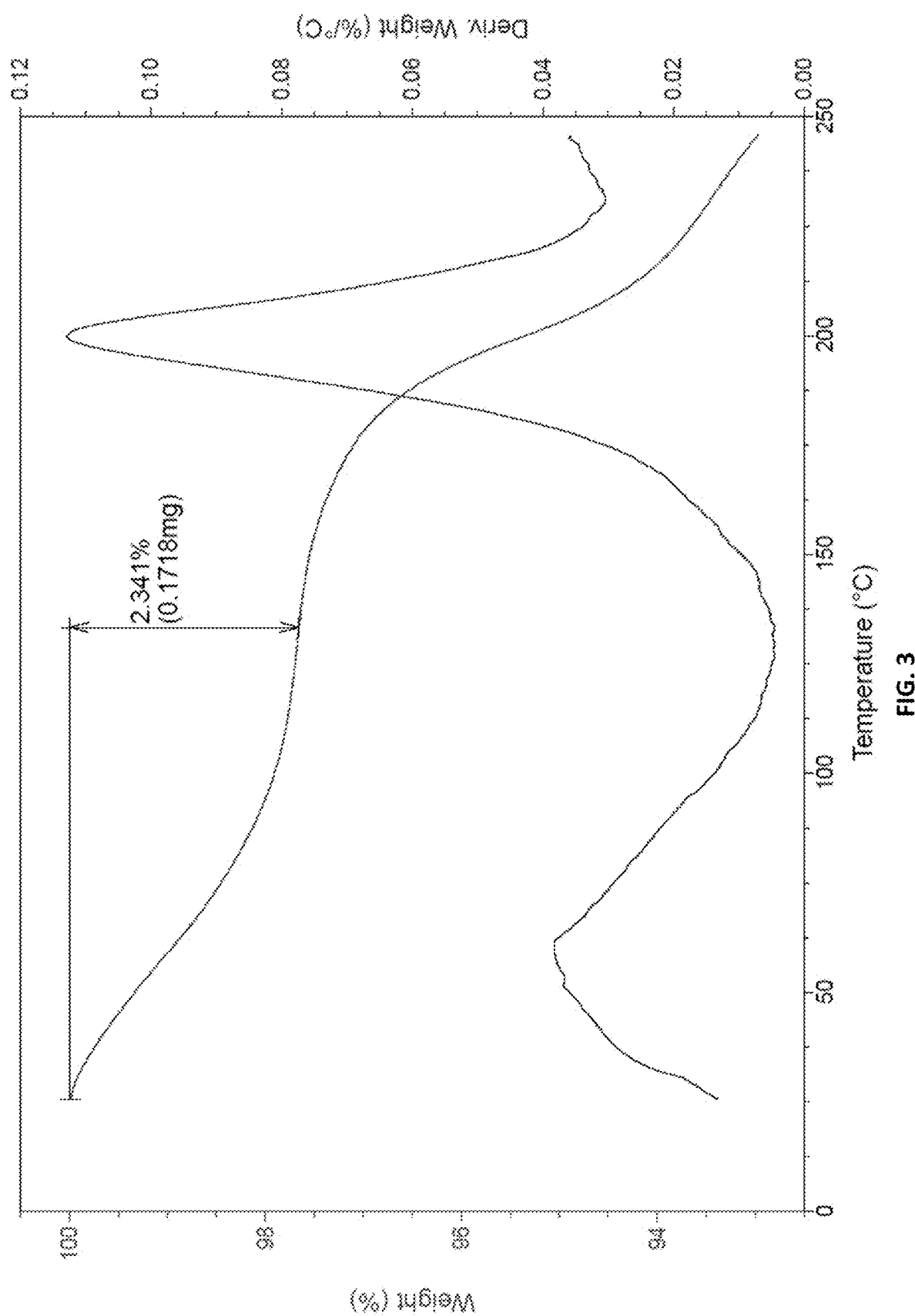
FIG. 3 is the characteristic thermogravimetric analysis (TGA) of nilotinib hydrochloride Form L.

In another embodiment, the present invention provides nilotinib hydrochloride Form L characterized by a thermogravimetric analysis (TGA) substantially in accordance with FIG. 3.

In another embodiment, the present invention provides nilotinib hydrochloride Form L characterized by a thermogravimetric analysis (TGA) showing weight loss of about 2.3%.

Figure 6:
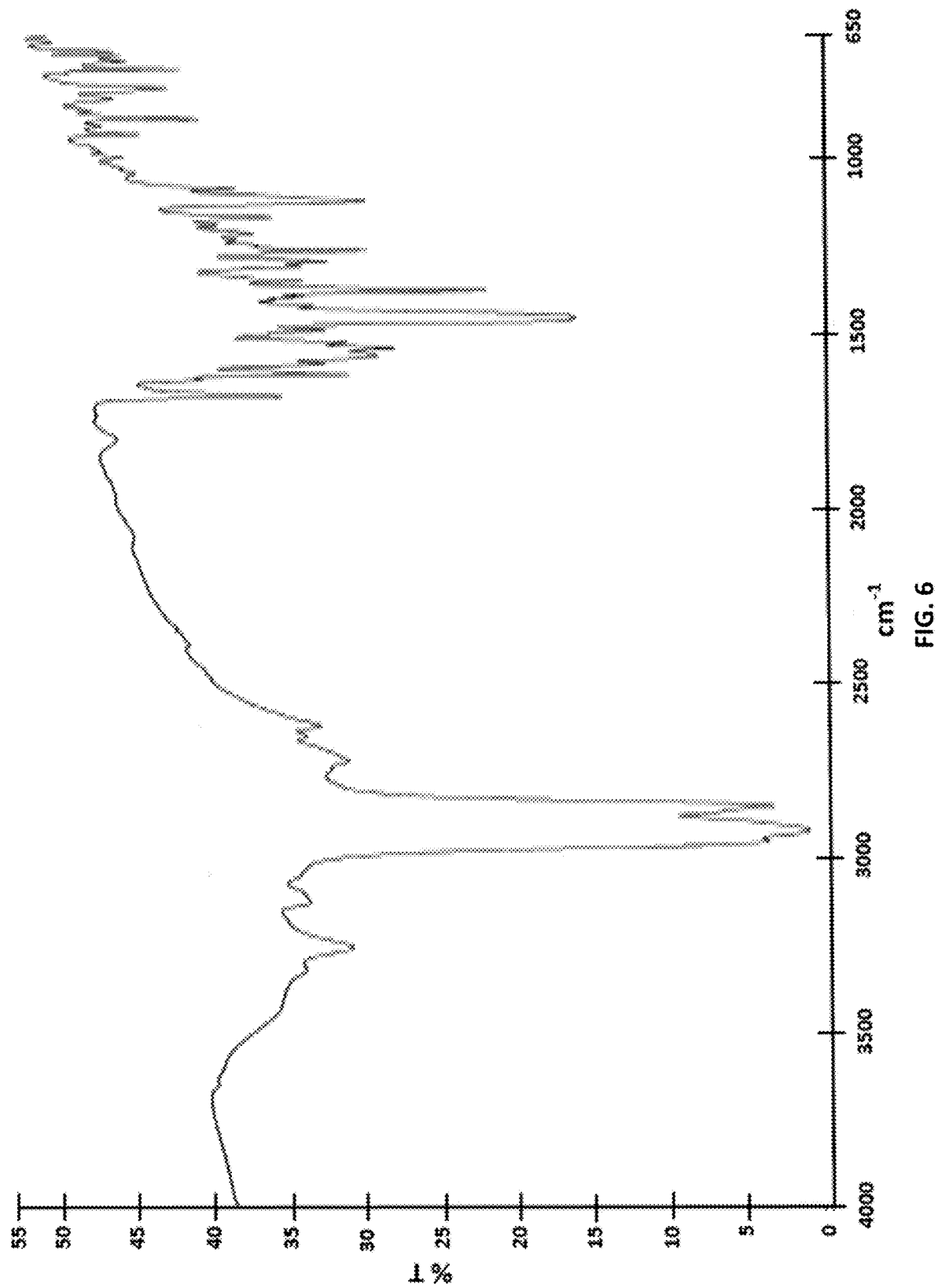
FIG. 6 is the characteristic Fourier-transform Infrared (FTIR) spectrum of nilotinib hydrochloride Form L.

In another embodiment, the present invention provides nilotinib hydrochloride Form L characterized by a Fourier-transform Infrared (FTIR) spectrum substantially in accordance with FIG. 6.

Figure 7:
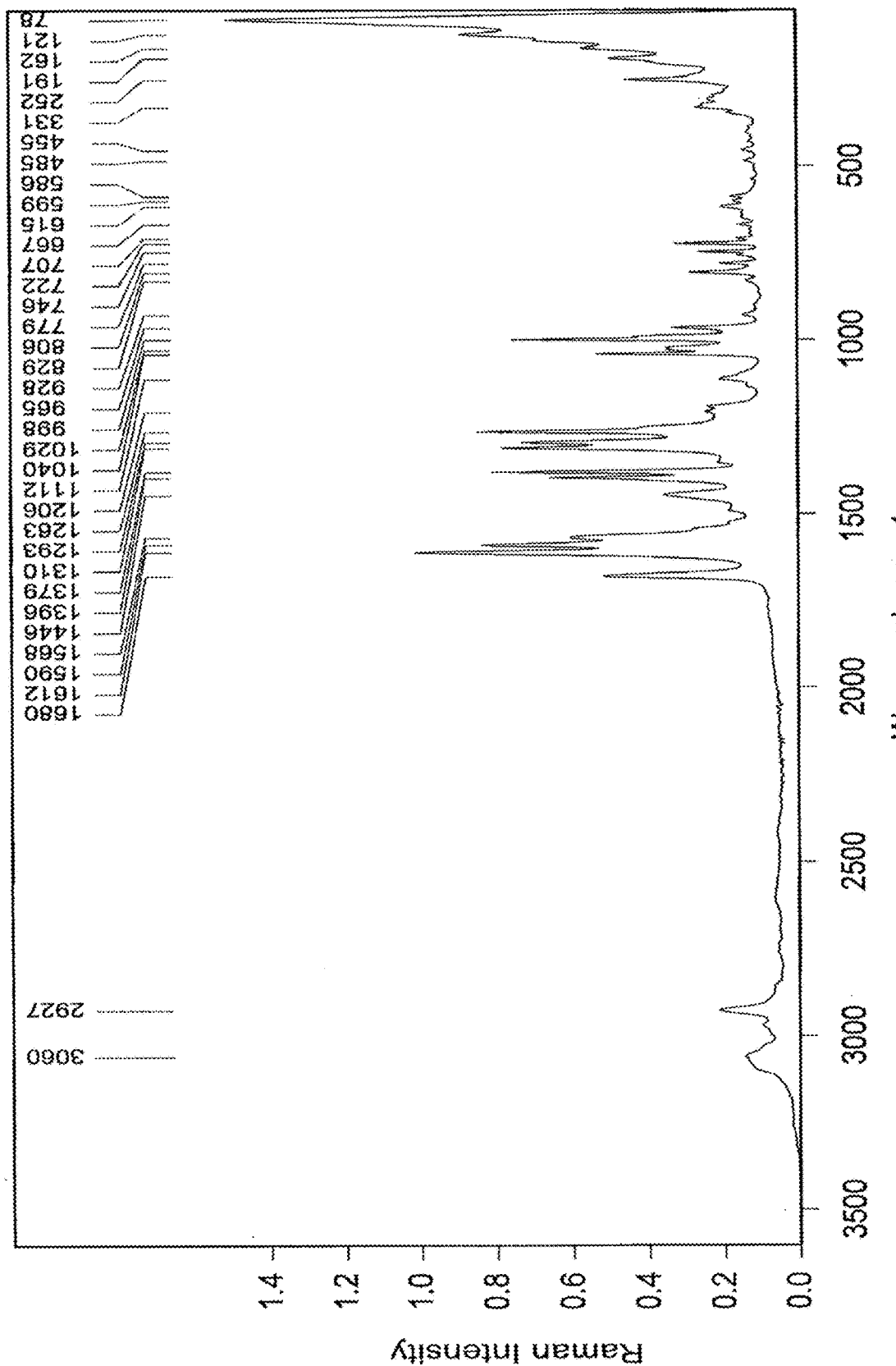
FIG. 7 is the characteristic Fourier-transform Raman spectrum of nilotinib hydrochloride Form L.

In another embodiment, the present invention provides nilotinib hydrochloride Form L characterized by Fourier-transform Raman spectrum substantially in accordance with FIG. 7.

In another embodiment, the present invention provides nilotinib hydrochloride Form L characterized by data selected from the group comprising: a powder X-Ray diffraction (PXRD) pattern substantially in accordance with FIG. 4; a differential scanning calorimetry (DSC) substantially in accordance with FIG. 2; a thermogravimetric analysis (TGA) substantially in accordance with FIG. 3; and combinations thereof.

In another embodiment, the present invention provides nilotinib hydrochloride Form L characterized by data selected from the group comprising: a powder X-Ray diffraction (PXRD) pattern substantially in accordance with FIG. 4; a differential scanning calorimetry (DSC) substantially in accordance with FIG. 5; a thermogravimetric analysis (TGA) substantially in accordance with FIG. 3; and combinations thereof.

In another embodiment, the present invention provides a process for the preparation of nilotinib hydrochloride Form L, which comprises of
  a) dissolving nilotinib in a mixture of formic acid and ethylformate at a suitable temperature,
  b) adding hydrochloric acid to step a) solution at a suitable temperature, and c) isolating nilotinib hydrochloride Form L.

In step a) of the aforementioned process, the dissolution of nilotinib is carried out at a suitable temperature of about 20° C. to reflux, preferably at about 25° C. to about 75° C., and more preferably at about 25° C. to about 35° C.

In step b) of the aforementioned process, the addition of hydrochloric acid to step a) solution can be carried out at a suitable temperature of about 5° C. to about 45° C.; preferably, the step a) solution is cooled to about 10° C. to about 15° C. before addition of hydrochloric acid.

Optionally, after the addition of hydrochloric acid, the step b) reaction mass is further diluted by adding additional ethylformate followed by seeding with Nilotinib hydrochloride Form L. Then the reaction mass is stirred for a sufficient period to time at a suitable temperature for complete precipitation; preferably, the reaction mass is maintain for about 20 to 28 hrs at about 5° C. to about 15° C.; and more preferably maintain for about 22-24 hrs at about 10° C. to about 15° C.

In step c) of the aforementioned process, the isolation of nilotinib hydrochloride Form L from the reaction mass can be carried out by any conventional techniques known in the art, for example filtration of the solid followed by washing with ethylformate.

The obtained solid nilotinib hydrochloride Form L may be further dried at about 25° C. to about 140° C. for sufficient period of time under atmospheric pressure or under reduced pressure. For example, the nilotinib hydrochloride can be dried initially at 25-35° C. for 4-6 hrs under reduced pressure and then dried at about 50° C. to about 70° C. for sufficient period of time.

As used herein in this specification, unless otherwise specified, nilotinib, which is used as a starting material is known in the art and can be prepared by the process described in any methods known in art, for example nilotinib may be synthesized as disclosed in PCT publication No: WO2004005281. The starting nilotinib may be in any form such as crude obtained directly from the reaction mass, crystalline, amorphous or other forms of nilotinib, including various solvates and hydrates known in the art.

In another embodiment, the present invention provides a pharmaceutical composition comprising novel crystalline nilotinib hydrochloride Form L of the present invention and at least one pharmaceutically acceptable excipient.

Nilotinib hydrochloride is currently marked under the brand name TASIGNA®, wherein Nilotinib hydrochloride is present in crystalline monohydrate form and the same is described as Form B in U.S. Pat. No. 8,415,363. Further, the said patent also discloses the characteristic details such as PXRD, FTIR, FT-Raman, DSC, TGA thermogram of crystalline Form B of nilotinib hydrochloride monohydrate. The said crystalline Form B of nilotinib hydrochloride present in commercial tablet and crystalline nilotinib hydrochloride Form L of the present invention are different, as both having different physio chemical characteristics/properties as described below;

Powder X-Ray Diffraction (PXRD) Pattern

The comparison PXRD pattern of Form L of the present invention with the Form B of the U.S. Pat. No. 8,415,363 indicates that both PXRD patterns are different from each other. Further, the comparison of 2 theta value of Form L with those of Form B disclosed in U.S. Pat. No. 8,415,363 indicates that number of 2θ peaks such as 9.2°, 11.4°, 12°, 14.6°, 23.9° and 27°, which including 100% relative intensity peak at 9.2° were absent in Form L. In addition, Form L of the present invention having additional characteristic peaks at about 4.9, 5.5, 8.9, 9.9, 11, 13.3, 17.8, 19.9, 21.1, 21.5, 22.9, 26.6, 27.6, 28.7 and 29.5° 2θ, where all the peak values listed are ±0.2° 2θ in comparison to Form B.

The Differential Scanning Calorimetry (DSC)

The DSC traces of Form L of the present invention shows three endotherms which are 90° C.-105° C., ~203° C. and ~224° C. The first endotherm which is quite broad and is due to the loss of free water and occurs at about 90° C.-105° C., the second one occurs at ~203° C., while the third one occurs at about 224° C. corresponding to the melting of free base, which is occurred due to losing of hydrochloride (see Figure-5). However, the DSC trace of Form B disclosed as FIG. 11 in U.S. Pat. No. 8,415,363 is different, which shows two endotherms; the first one occurring as sharp band at about 100° C.-120° C. corresponds to dehydration of free water, leading to the formation of the anhydrate form (characterized & designated as Form B' in U.S. Pat. No. 8,415,363), while the second one occurring at about 190° C. corresponds to the melting of Form B'. In Form L, first endotherm at about 100° C. corresponds to the loss of water is very broad in comparison to the Form B where water loss occurs at higher temperature of 130° C. with a relatively sharp endotherm (30° C. higher than corresponding water loss temperature of Form L), which indicates that the water in Form L is either a loosely bound water, or surface or absorbed water rather than bounded crystalline water in Form B.

Thermogravimetric Analysis (TGA)

TGA traces of Form L of the present invention shown in FIG. 3 and TGA traces of Form B of nilotinib hydrochloride monohydrate disclosed as FIG. 11 in U.S. Pat. No. 8,415,363. In Form L, a gradual weight loss of about 2.5% between about 28° C. to about 140° C. corresponds to the loss of water, whereas Form B has a relatively steeper slope with a weight loss of about 3.0% in the range of about 25° C. to about 140° C. corresponding to about 1 mole equivalent of water loss and its similar to theoretical amount of water in monohydrate is 3.1%. Thus the above comparison TGA results indicates that about 2.5% water loss found in Form L can be either loosely bound crystalline water or surface or absorbed water.

In addition, the following table shows the comparison of thermogravimetric studies at specific temperature range as mentioned for Form B of nilotinib hydrochloride in table 22 of U.S. Pat. No. 8,415,363 with the Form L of the present invention;

| Loss on drying | Form B (U.S. Pat. No. 8,415,363) | Form L | Remarks |
| --- | --- | --- | --- |
| 30° C.-100° C. | 1.00% | 2.3% | The weight loss 1% in Form B and 2.3% in Form L corresponds to free water loss. |
| 100° C.-220° C. | 3.02% | 7.3% | The weight loss 3.02% in Form B corresponds to loss of bounded crystalline water; whereas the weight loss of 7.3% in Form L corresponds to loss of HCl. |

Fourier-Transform Infrared (FTIR) Spectrum

Figure 9:
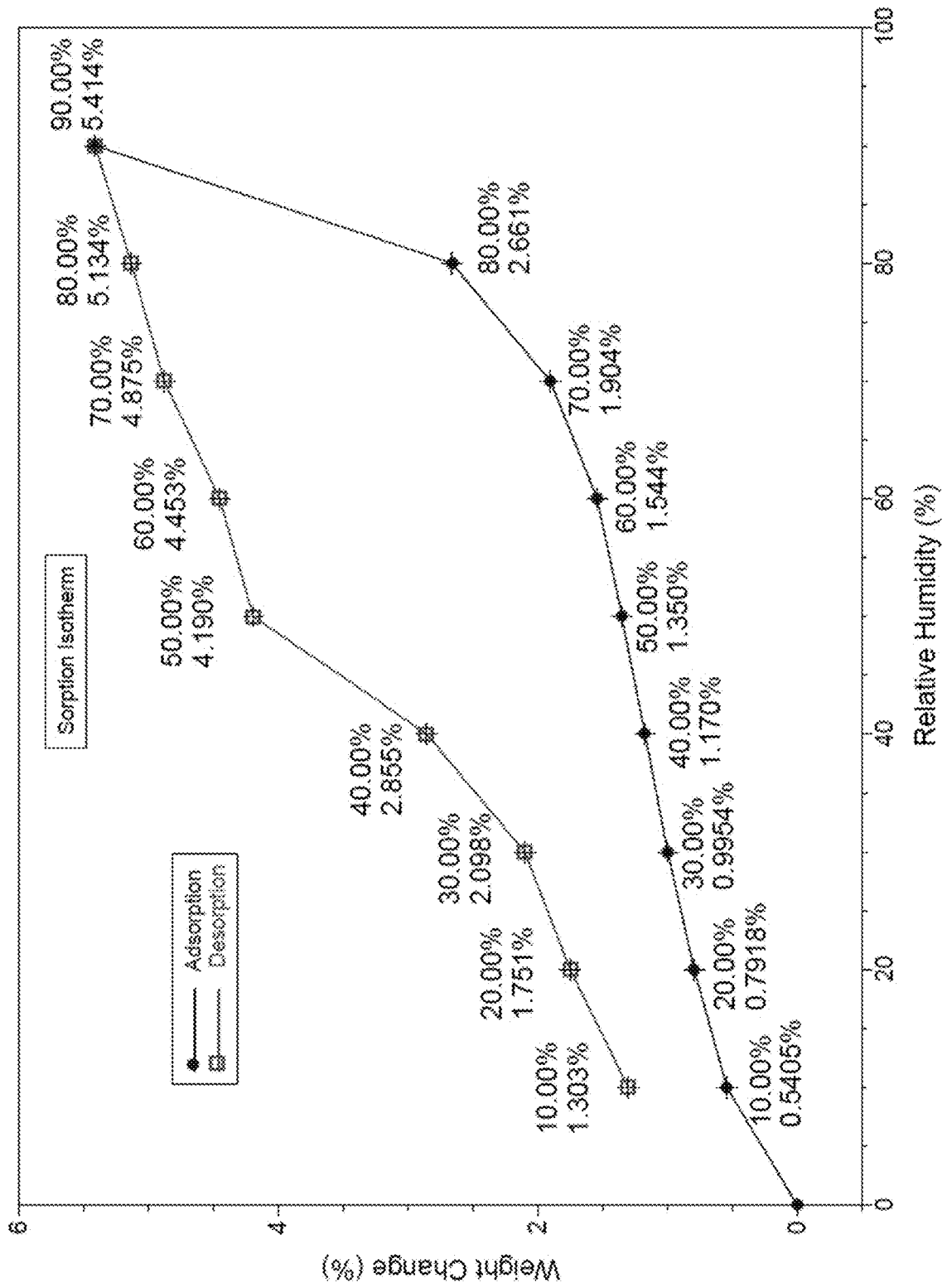
FIG. 9 shows Dynamic Vapour sorption isotherm of nilotinib hydrochloride Form L.

FT-IR spectrum of Form L of the present invention is shown in Figure-6 and FT-IR spectrum of Form B was disclosed as FIG. 9 in U.S. Pat. No. 8,415,363 and the corresponding FT-IR bands values of both forms shown in the below table.

| Polymorph | FT-IR bands (cm$^{-1}$) |
|---|---|
| Form L | 3323, 3258, 3128, 2953, 2854, 2723, 2652, 2624, 2390, 1805, 1679, 1632, 1617, 1587, 1564, 1542, 1526, 1491, 1456, 1422, 1405, 1395, 1377, 1352, 1309, 1295, 1264, 1250, 1236, 1216, 1192, 1169, 1121, 1087, 1043, 1028, 997, 976, 929, 906, 886, 861, 828, 798, 745, 721, 708, 693 and 667 cm$^{-1}$ |
| Form B (U.S. Pat. No. 8,415,363) | 3211, 3058, 2925, 2854, 1676, 1614, 1587, 1454, 1411, 1378, 1343, 1304, 1279, 1263, 1230, 1197, 1181, 1120, 1089, 1046, 1033, 1005, 905, 892, 874, 801, 755, 706 and 695 cm$^{-1}$ |

The comparison of FT-IR band values of Form L with Form B shows that seven characteristic FT-IR bands of Form B, which includes 2925, 1343, 1279, 1181, 1033, 874, and 755 cm$^{-1}$ are absent in Form L, indicating that these forms have distinct FT-IR characteristics.

Fourier-Transform Raman Spectrum

Figure 10:
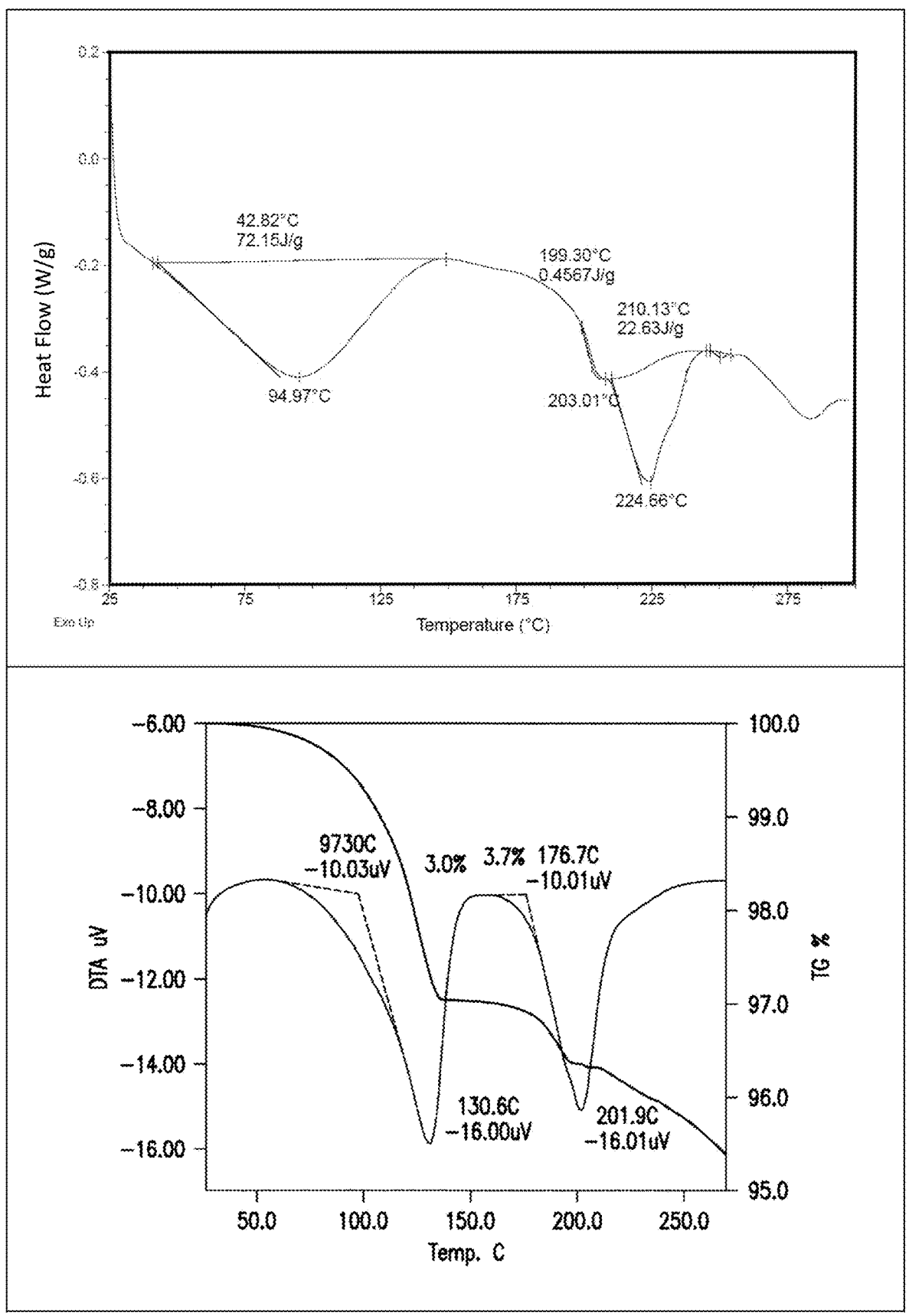
FIG. 10 shows comparison of differential scanning calorimetric (DSC) thermogram of Nilotinib hydrochloride Form L (top) and Nilotinib hydrochloride monohydrate Form B (bottom).

FT-Raman spectrum of Form L of the present invention shown in Figure-7 and FT-Raman spectrum of Form B was disclosed as FIG. 10 in U.S. Pat. No. 8,415,363 and the corresponding FT-Raman band values of both forms shown in the below table.

| Polymorph | FT-Raman bands (cm$^{-1}$) |
|---|---|
| Form L | 3060, 2927, 1680, 1612, 1590, 1568, 1446, 1396, 1379, 1310, 1293, 1263, 1206, 1112, 1040, 1029, 998, 965, 928, 829, 806, 779, 746, 722, 707, 667, 615, 599, 586, 485, 455, 331, 252, 191, 162, 121 & 78 cm−1 |
| Form B (U.S. Pat. No. 8,415,363) | 3078, 3026, 2975, 2930, 1672, 1610, 1602, 1593, 1541, 1476, 1451, 1400, 1385, 1332, 1303, 1263, 1251, 1210, 1089, 1046, 1033, 851, 802, 755, 660, 483, 456, 395, 355, 317, 217, 243, 198, 160, 148 & 114 cm−1 |

The comparison of FT-Raman band values of Form L with Form B shows that twelve characteristic FT-Raman bands of Form B which include 2854, 1411, 1343, 1279, 1197, 1181, 1089, 1033, 905, 892 and 874 cm$^{-1}$ are absent in Form L, indicating that Form L is different from Form B.

Dynamic Vapour Sorption (DVS)

The Dynamic Vapour sorption isotherm of nilotinib hydrochloride Form L of the present invention is shown in FIG. 9; whereas the corresponding data of adsorption and desorption weight changes of Form L shown in the below table:

| Adsorption | | | | | | | | | |
|---|---|---|---|---|---|---|---|---|---|
| % RH | 10 | 20 | 30 | 40 | 50 | 60 | 70 | 80 | 90 |
| % Weight change | 0.5405 | 0.7918 | 0.9954 | 1.170 | 1.350 | 1.544 | 1.904 | 2.661 | 5.414 |

| Desorption | | | | | | | | | |
|---|---|---|---|---|---|---|---|---|---|
| % RH | 90 | 80 | 70 | 60 | 50 | 40 | 30 | 20 | 10 |
| % Weight change | 5.414 | 5.134 | 4.875 | 4.453 | 4.190 | 2.855 | 2.098 | 1.751 | 1.303 |

There is a difference of about 3% in water content between absorption and desorption of water by Form L between 50% and 60% RH at room temperature (RT) after going through a maximum absorption of about 5.4% at 90% RH, indicating that the sample has a tendency to pick up or hold up to about 3% water under ambient conditions. In addition, the fact that Form L has a tendency to pick up about 2.7% water at 80% RH at RT indicates that it is moderately hygroscopic. Thus the DVS analysis indicates that the water content in Form L is more likely to be a surface or absorbed water.

Variable Temperature Powder X-Ray Diffraction (VT-PXRD)

Figure 8:
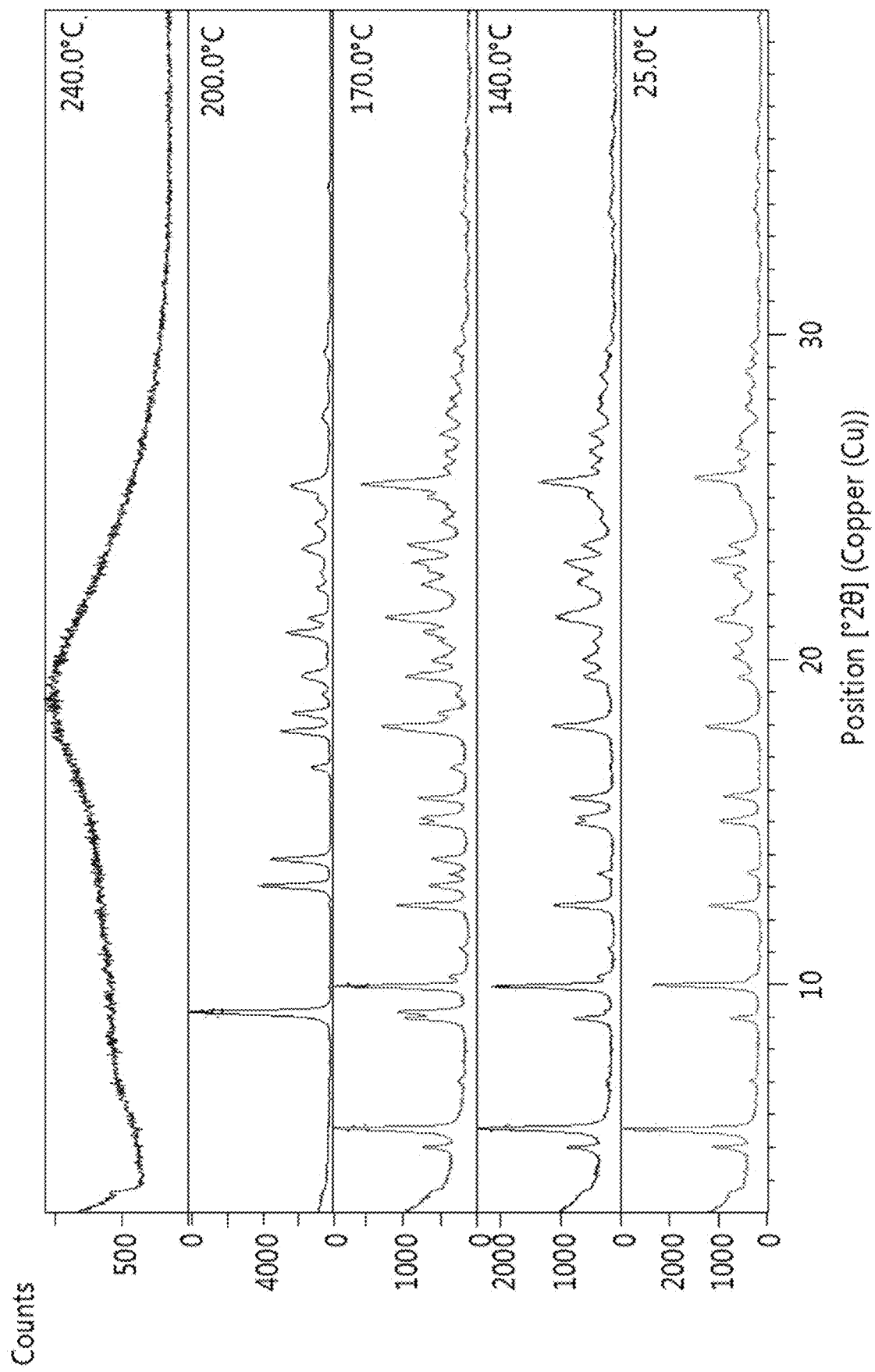
FIG. 8 shows thermally induced phase transition of Nilotinib hydrochloride Form L by variable temperature powder X-ray diffraction (VT-PXRD).

TGA, DSC and DVS analysis of Form L as discussed above indicates that the water present in Form L may be the surface water or absorbed water rather than bounded water. In order to further confirm the role of water in Form L, Variable temperature-PXRD of Form L of the present invention was carried out in the temperature range of 25-300° C. with a heating rate of 10° C./mins and the corresponding VT-PXRD shown in Figure-8.

Form L of the present invention retain its characteristic PXRD up to about 140° C. and new phase started appearing after 140° C. and peaks related to Form L almost disappeared at about 200° C. and beyond 240° C. only amorphous form found to be exist during VT-PXRD study. The PXRD of new phase is found to be virtually similar to that of Nilotinib free base Form A as described in FIG. 1 of U.S. Pat. No. 8,415,363, which indicates that free base Form A is formed due to loss of HCl between 140° C.-200° C. in Form L. However which is in contrast to VT-PXRD of Form B of nilotinib hydrochloride as described in U.S. Pat. No. 8,415,363, where Form B monohydrate converted into Form B' (anhydrate) due to loss of the crystalline water between 145° C.-195° C. and then transformed to an amorphous phase after melting at 195° C.

It is clear from VT-PXRD study that crystalline Form L is not a hydrate as no significant structural changes were observed between 25° C. to 140° C. corresponding to the water loss and moreover crystalline Form L does not form any intermediary anhydrous form due to the loss of bounded water as in Form B, instead losing hydrochloride at a temperature of 140-200° C. as there is no bounded water in Form L and directly converted into amorphous form.

EXAMPLES

The following non-limiting examples illustrate specific embodiments of the present invention. They are not intended to be limiting the scope of the present invention in any way.

Example-1: Preparation of Nilotinib Hydrochloride Form L

Nilotinib (20 g) was dissolved in a mixture of formic acid (40 mL) and ethyl formate (60 mL) at 23-27° C. Concentrated hydrochloric acid (3.24 mL) was added to the above solution at 23-27° C. and stirred for 5 mins at the same temperature. Ethyl formate (340 mL) was added to the reaction mass and stirred for 16 hrs at 23-27° C. The solid obtained was filtered, washed with ethyl formate and suck dried. The suck dried material was further dried at room temperature under vacuum for 6 hrs followed by dried at 120° C. in hot air oven for 13 hrs to get the title compound. Yield: 18.4 g The XRPD is set forth in FIG. 1; the DSC is set forth in FIG. 2 and the TGA is set forth in FIG. 3.

Example-2: Preparation of Nilotinib Hydrochloride Form L

Nilotinib (20 g) was dissolved in a mixture of formic acid (40 mL) and ethyl formate (60 mL) at 23-27° C. Concentrated hydrochloric acid (3.24 mL) was added to the above solution at 23-27° C. and stirred for 5 mins at the same temperature. Ethyl formate (340 mL) was added to the reaction mass and stirred for 16 hrs at 23-27° C. The solid obtained was filtered, washed with ethyl formate and suck dried. The suck dried material was further dried at RT under vacuum for 6 hrs followed by dried at 120° C. in hot air oven for 13 hrs to get the title compound. Yield: 19.2 g Example-3: Preparation of Nilotinib Hydrochloride Form L Nilotinib (20 g) was dissolved in a mixture of formic acid (40 mL) and ethyl formate (60 mL) at 23-27° C. Concentrated hydrochloric acid (3.24 mL) was added to the above solution at 23-27° C. and stirred for 5 mins at the same temperature. Ethyl formate (540 mL) was added to the reaction mass and stirred for 16 hrs at 23-27° C. The solid obtained was filtered, washed with ethyl formate and suck dried. The suck dried material was further dried initially at 48-52° C. for 3 hrs, then at 83-87° C. for 4 hrs under vacuum, and finally dried at 120° C. in hot air oven for 13 hrs to get the title compound. Yield: 18.6 g Example-4: Preparation of Nilotinib Hydrochloride Form L Nilotinib (100 g) was dissolved in a mixture of formic acid (200 mL) and ethyl formate (300 mL) at 25-35° C. and the obtained solution was cooled to 9-15° C. concentrated hydrochloric acid (18.9 g) was added to the above solution over a period of 30 mins at 9-15° C. and stirred for 20 mins at the same temperature. Ethyl formate (1400 mL) was added to the reaction mass at 9-15° C. followed by seeded with Nilotinib hydrochloride Form L (300 mg) and stirred for 24 hrs at 9-15° C. The precipitated solid was filtered, washed with ethyl formate and suck dried. The suck dried material was further dried initially at 25-35° C. for 6 hrs, then at 57-63° C. in a Fluidized Bed Dryer for 25 hrs to get the title compound. Yield: 90 g.

The XRPD is set forth in FIG. 4, the DSC is set forth in FIG. 5 and the TGA is set forth in FIG. 3.

Example-5: Preparation of Nilotinib Hydrochloride Form L

Nilotinib (100 g) was dissolved in a mixture of formic acid (200 mL) and ethyl formate (300 mL) at 25-35° C. and the obtained solution was cooled to 9-15° C. concentrated hydrochloric acid (18.9 g) was added to the above solution over a period of 30 mins at 9-15° C. and stirred for 20 mins at the same temperature. Ethyl formate (1400 mL) was added to the reaction mass at 9-15° C. and stirred for 24 hrs at 9-15° C. The precipitated solid was filtered, washed with ethyl formate and suck dried. The suck dried material was further dried initially at 25-35° C. for 6 hrs, then at 57-63° C. in a Fluidized Bed Dryer for 25 hrs to get the title compound. Yield: 85 g.

The XRPD is set forth in FIG. 4, the DSC is set forth in FIG. 5 and the TGA is set forth in FIG. 3.

Example-6: Stability Study Details

The following stability study data tables at different storage condition ensures that the Nilotinib hydrochloride Form L of the present invention retained the same polymorphic and chemical identity at least up to two months.

Nilotinib hydrochloride Form L is packed in a transparent Low density polyethylene (LDPE) bag with a strip seal along with nitrogen filling, which is again kept in a second transparent low density polyethylene bag with strip seal. The LDPE bag is kept in to a triple laminated sunlight barrier with heat seal followed by in a high density polyethylene container and well closed.

Alternatively, Nilotinib hydrochloride Form L is packed in a HM LDPE bag in nitrogen atmosphere, fill the bag with nitrogen and seal it with vacuum sealer. Place this bag in another HM LDPE bag, fill with nitrogen, keep one silica gel packet between two bags and seal the bag with vacuum sealer. Place this in a triple laminated sunlight barrier bag, seal the bag with vacuum sealer; and finally kept it in a HDPE container.

TABLE I

Chemical and polymorphic stability data of Nilotinib hydrochloride Form L when stored at 25 ± 2° C./60 ± 5% RH:

| Parameters | Initial (% by HPLC) | 2 month (% by HPLC) |
|---|---|---|
| Description | Slightly yellow color solid | Slightly yellow color solid |
| Acid impurity (Imp-1) | ND | ND |
| Methyl ester impurity (Imp-2) | ND | ND |
| Des-methyl analogue (Imp-3) | ND | ND |
| 5-Methyl isomer (Imp-4) | ND | BDRL |
| 4-Ethyl analogue (Imp-5) | BDRL | BDRL |
| Any unspecified impurity | BDRL | BDRL |
| Total Impurities | BDRL | BDRL |
| Solid form by XRD | Complies | Complies |

ND: Not detected;
BDRL: Below disregard limit

TABLE II

Chemical and polymorphic stability data of Nilotinib hydrochloride Form L when stored at 40 ± 2° C./75 ± 5% RH:

| Parameters | Initial (% by HPLC) | 1 month (% by HPLC) | 2 month (% by HPLC) |
|---|---|---|---|
| Description | Slightly yellow color solid | Slightly yellow color solid | Slightly yellow color solid |
| Acid impurity (Imp-1) | ND | BDRL | ND |
| Methyl ester impurity (Imp-2) | ND | BDRL | ND |
| Des-methyl analogue (Imp-3) | ND | ND | ND |
| 5-Methyl isomer (Imp-4) | ND | BDRL | BDRL |
| 4-Ethyl analogue (Imp-5) | BDRL | BDRL | BDRL |
| Any unspecified impurity | BDRL | BDRL | BDRL |
| Total Impurities | BDRL | BDRL | BDRL |
| Solid form by XRD | Complies | Complies | Complies |

ND: Not detected;
BDRL: Below disregard limit
Imp-1: 4-Methyl-3-{[4-(3-pyridinyl)-2-pyrimidinyl]amino}benzoic acid;
Imp-2: Methyl4-methyl-3-[[4-(pyridin-3-yl)pyrimidin-2-yl]amino]benzoate;
Imp-3: N-[3-(1H-imidazol-1-yl)-5-(trifluoromethyl)phenyl]-4-methyl-3-[[4-(pyridin-3-yl)pyrimidin-2-yl]amino]benzamide;
Imp-4: 4-methyl-N-[3-(5-methyl-1H-imidazol-1-yl)-5-(trifluoromethyl)phenyl]-3-[[4-(pyridin-3-yl)pyrimidin-2-yl]amino]benzamide;
Imp-5: N-[3-(4-ethyl-1H-imidazol-1-yl)-5-(trifluoromethyl)phenyl]-4-methyl-3-[[4-(pyridin-3-yl)pyrimidin-2-yl]amino] benzamide.

The Nilotinib hydrochloride Form L was analysed using High Performance Liquid Chromatography ("HPLC") with the conditions as tabulated below:

| Column | Halo C18, (150 × 4.6) mm |
|---|---|
| Column temp | 30° C. |
| Mobile phase | buffer and acetonitrile |
| Diluent | Methanol and acetonitrile |
| Flow rate | 0.7 ml/min |
| Wavelength | 240 nm |
| Injection Volume | 10 µl |

Example-7: Solubility Studies

Saturation solubility studies were conducted in various mediums for nilotinib hydrochloride Form L of the present invention and nilotinib hydrochloride monohydrate Form B (U.S. Pat. No. 8,415,363).

TABLE III

Comparative Saturation Solubility data of Form L and nilotinib hydrochloride monohydrate (Form B) (approximately at 25° C., mg/ml).

| Conditions | HCl monohydrate (Form B) | Form L |
|---|---|---|
| 0.1N HCl | 0.94 | 1.86 |
| 0.01N HCl | 0.08 | 0.17 |
| Phosphate buffer, pH 6.8 | Below detection | 0.02 |
| Water | 0.17 | 0.16 |
| Ethanol | 3.69 | 16.29 |
| Isopropanol | 1.93 | 2.74 |
| Thermogravimetric (weight loss %) (10° C./minute) | 0.91 (RT to 80° C.) | 1.6 (RT to 80°) |

From the above data it is observed that novel polymorphic Form L shows better solubility when compared to Form B.

We claim:

1. Crystalline nilotinib hydrochloride Form L characterized by a powder X-Ray diffraction pattern having at least six peaks selected from 4.9, 5.5, 6.9, 8.9, 9.9, 11, 13.3, 17.8, 19.9, 21.1, 21.5, 22.9, 26.6, 27.6, 28.7, and 29.5° 2θ, where all the peak values listed are ±0.2° 2θ.

2. The crystalline nilotinib hydrochloride Form L according to claim 1, further characterized by a powder X-Ray diffraction pattern having at least three additional peaks selected from 6.9, 12.3, 14.9, 15.7, 19.3, 20.3, 22.0, 23.3, 24.8, 25.5, 26.0, 31.3, 33.7, 34.7, 35.5, 36.3 and 37.6° 2θ, where all the peak values listed are ±0.2° 2θ.

3. Crystalline nilotinib hydrochloride Form L, characterized by a powder X-Ray diffraction pattern having at least one peak at 4.9, 5.5, 6.9, 8.9, 9.9, 11, 12.3, 13.3, 14.9, 15.7, 17.8, 19.3, 19.9, 20.3, 21.1, 21.5, 22.0, 22.9, 23.3, 24.8, 25.5, 26.0, 26.6, 27.6, 28.7, 29.5, 31.3, 33 7, 34 7, 35.5, 36.3 and 37.6° 2θ, where all the peak values listed are ±0.2° 2θ, wherein the crystalline nilotinib hydrochloride Form L is further characterized by a powder X-Ray diffraction pattern substantially in accordance with FIG. 4.

4. A process for the preparation of crystalline nilotinib hydrochloride Form L, comprising:
  a) dissolving nilotinib in a mixture of formic acid and ethylformate at a temperature;
  b) adding hydrochloric acid to the step a) solution at a temperature; and
  c) isolating the nilotinib hydrochloride Form L.

5. The process as claimed in claim 4, wherein in step a) the temperature for dissolving nilotinib is about 20° C. to reflux.

6. The process as claimed in claim 4, wherein in step a) the temperature for dissolving nilotinib is about 25° C. to about 35° C.

7. The process as claimed in claim 4, wherein in step b) the temperature for addition of hydrochloric acid is about 5° C. to about 45° C.

8. The process as claimed in claim 4, wherein in step b) the temperature for addition of hydrochloric acid is about 10° C. to about 15° C.

9. The process as claimed in claim 4, further comprising, in the step b), adding ethyl formate to the reaction mass.

10. The process as claimed in claim 9, further comprising, in the step b), seeding the reaction mass with nilotinib hydrochloride Form L.

11. A pharmaceutical composition or dosage form comprising crystalline nilotinib hydrochloride Form L of claim 1 and at least one pharmaceutically acceptable excipient.

12. Crystalline nilotinib hydrochloride Form L, characterized by a powder X-Ray diffraction pattern having at least one peak at 4.9, 5.5, 6.9, 8.9, 9.9, 11, 12.3, 13.3, 14.9, 15.7, 17.8, 19.3, 19.9, 20.3, 21.1, 21.5, 22.0, 22.9, 23.3, 24.8, 25.5, 26.0, 26.6, 27.6, 28.7, 29.5, 31.3, 33.7, 34.7, 35.5, 36.3 and 37.6° 2θ, where all the peak values listed are ±0.2° 2θ, wherein the crystalline nilotinib hydrochloride Form L is further characterized by a thermogravimetric analysis (TGA) substantially in accordance with FIG. 3.

* * * * *